United States Patent [19]

Walkow

[11] Patent Number: 4,710,711
[45] Date of Patent: Dec. 1, 1987

[54] APPARATUS FOR NONDESTRUCTIVE TESTING OF SUBSURFACE PIPING USING THREE COILS WITH OPPOSING FIELDS

[75] Inventor: Arnold M. Walkow, Houston, Tex.

[73] Assignee: Western Atlas International, Inc., Houston, Tex.

[21] Appl. No.: 805,027

[22] Filed: Dec. 4, 1985

[51] Int. Cl.[4] ..................... G01N 27/72; G01N 27/82; G01R 33/12
[52] U.S. Cl. .................................. 324/221; 324/232; 324/346
[58] Field of Search ................................ 324/219–221, 324/232, 346, 367, 374; 166/66.5

[56] References Cited

U.S. PATENT DOCUMENTS

| | | | |
|---|---|---|---|
| 3,225,293 | 12/1965 | Wood et al. | 324/221 |
| 3,315,154 | 4/1967 | Nuttall | 324/232 |
| 3,393,732 | 7/1968 | Murphy, Jr. et al. | 324/221 |
| 3,437,810 | 4/1969 | Wood et al. | 324/221 |
| 3,449,662 | 10/1969 | Wood | 324/220 |
| 3,543,144 | 11/1970 | Walters et al. | 324/221 |
| 3,899,734 | 8/1975 | Beaver et al. | 324/220 |
| 3,940,689 | 2/1976 | Johnson, Jr. | 324/221 |
| 4,320,340 | 3/1982 | Lichtenberg | 324/221 |

Primary Examiner—Reinhard J. Eisenzopf
Assistant Examiner—Walter E. Snow
Attorney, Agent, or Firm—Patrick H. McCollum

[57] ABSTRACT

Method and apparatus for nondestructive inspection of oilfield piping includes first and second elongated nonmagnetic housing members having an elongated magnetic core therebetween. A first coil assembly for emitting a unidirectional flux field is coupled to the core member. Detector shoes are coupled to said core member proximate the first coil assembly and are based into contact with the interior surface of the piping. Second and third coil assemblies are coupled to the core member for emitting unidirectional fields in opposition to the field emitted from the first coil assembly.

3 Claims, 9 Drawing Figures

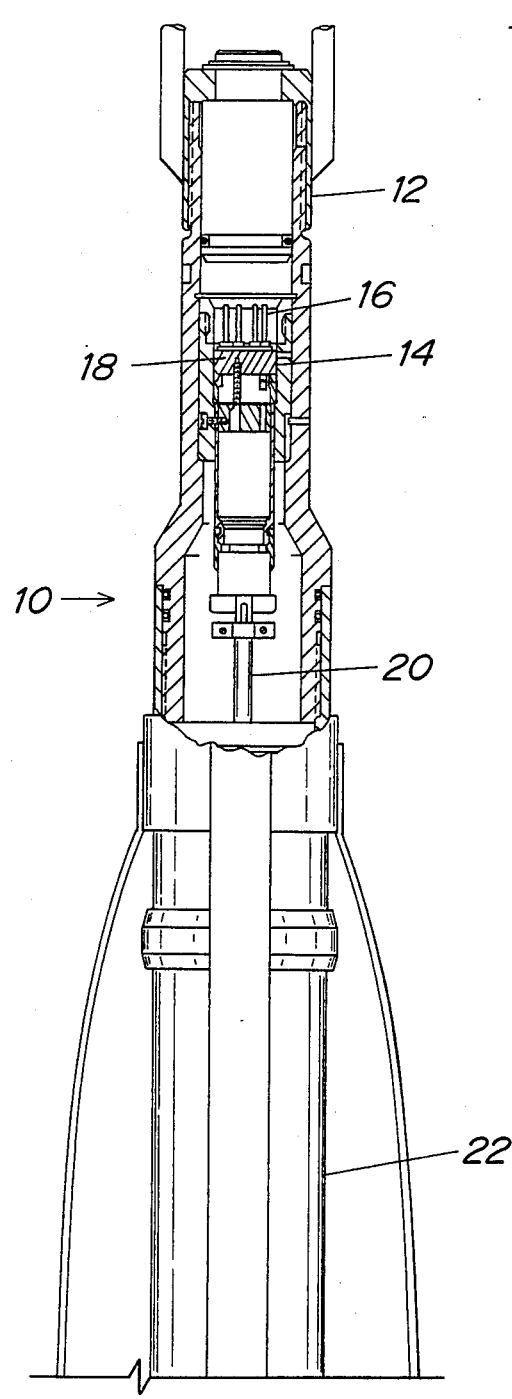
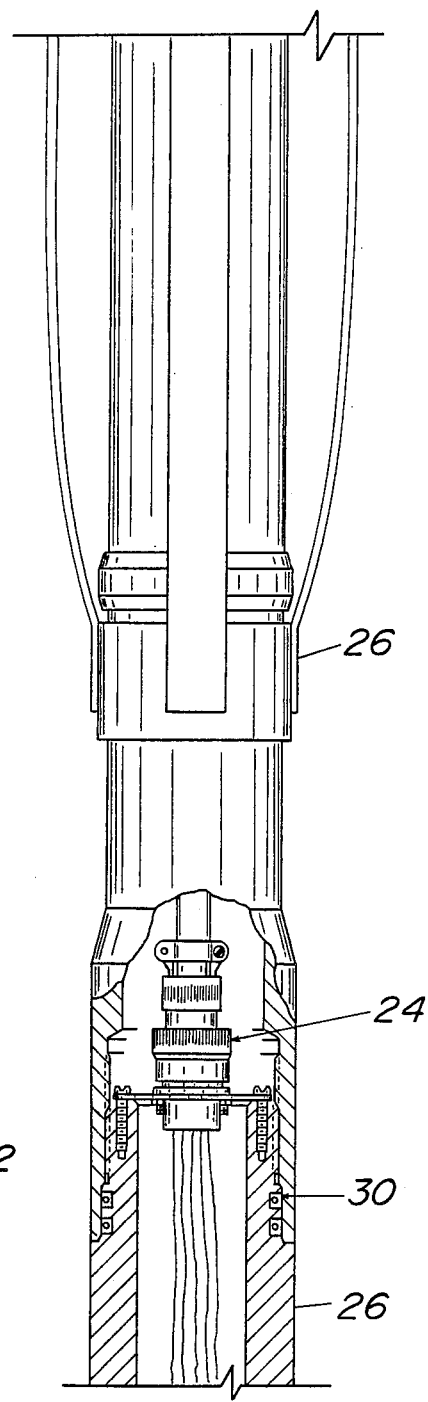
FIGURE 1a
FIGURE 1b

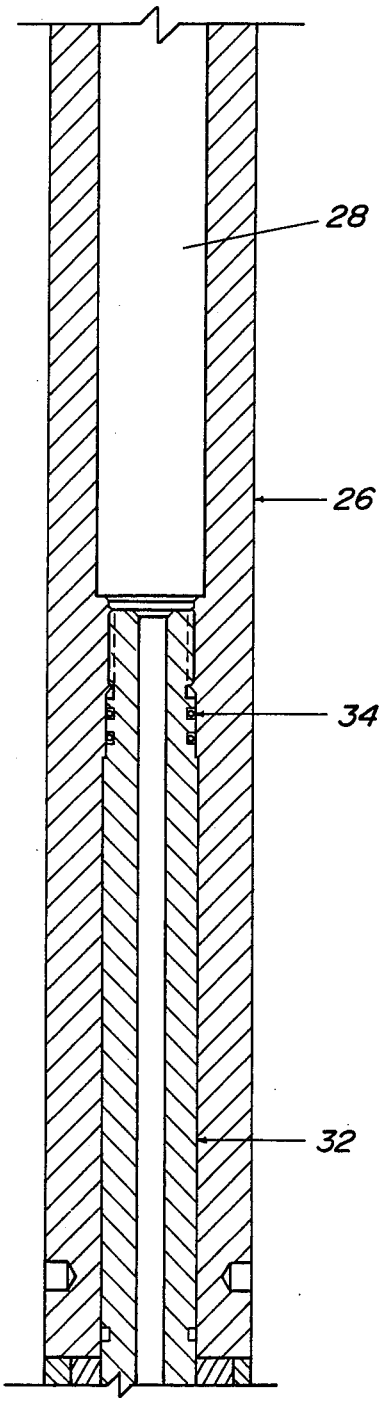
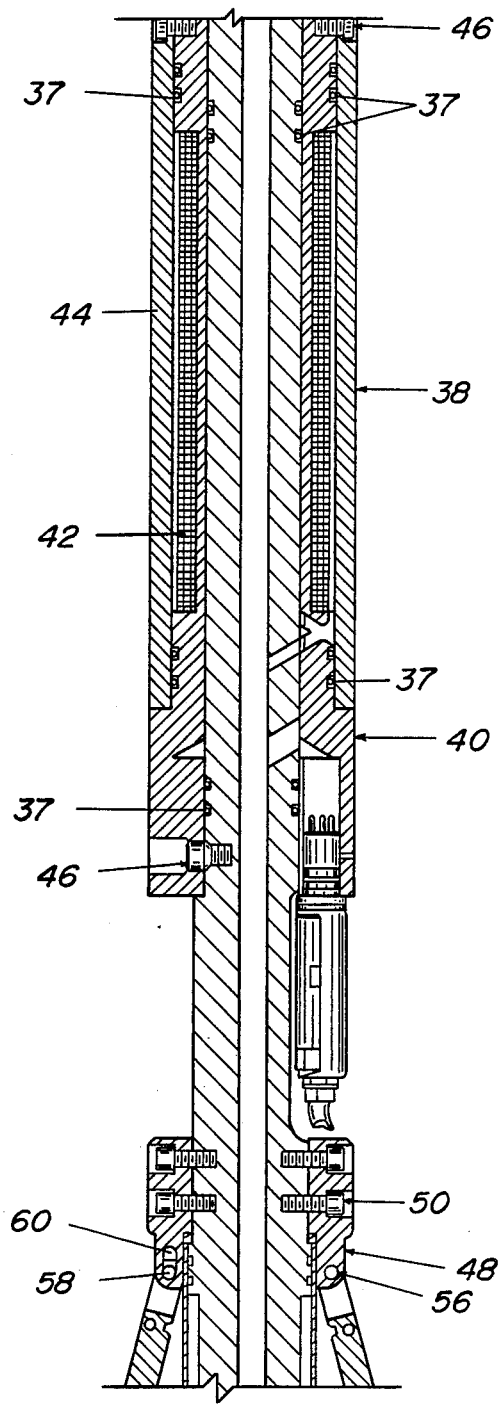
FIGURE 1c
FIGURE 1d

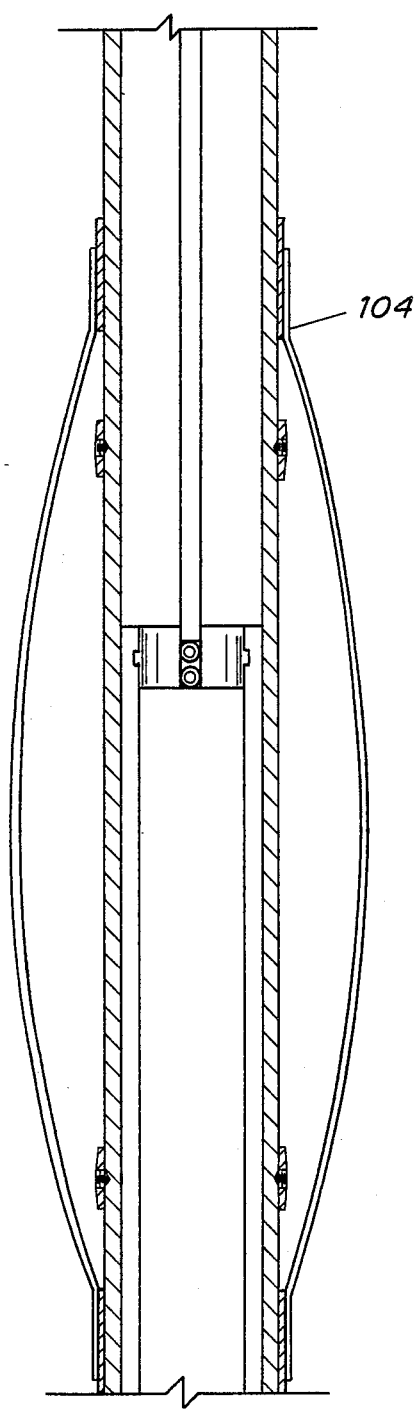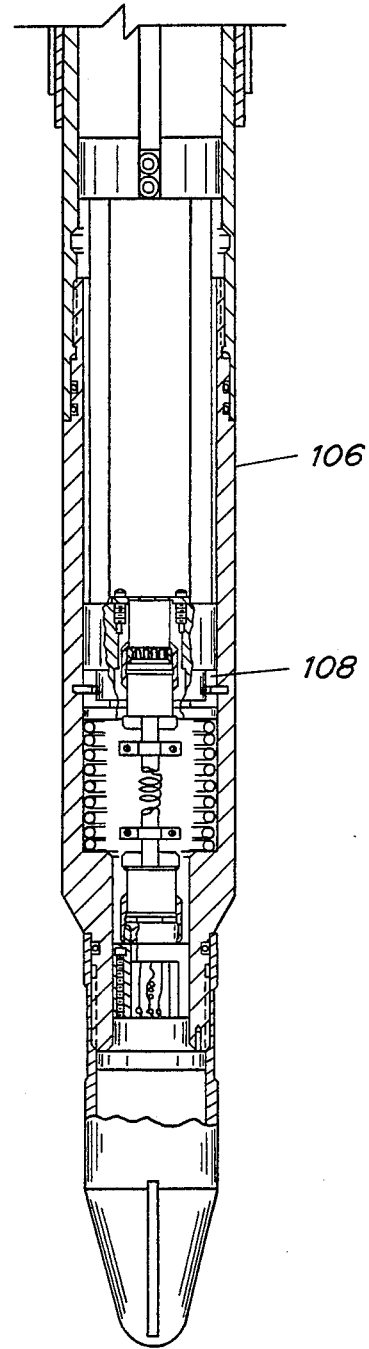
FIGURE 1h
FIGURE 1i

APPARATUS FOR NONDESTRUCTIVE TESTING OF SUBSURFACE PIPING USING THREE COILS WITH OPPOSING FIELDS

BACKGROUND OF THE INVENTION

This invention relates to improved methods and apparatus for evaluating the condition of subsurface oilfield piping and, more particularly, relates to apparatus for nondestructive testing of the state of deterioration of relatively small diameter subsurface tubing and casing.

It is common knowledge in the petroleum industry to use steel or iron pipe in nearly all oil and gas wells. Such piping serves several useful purposes including shutting off water bearing formations, preventing formation deterioration and shutting off intermediate oil or gas zones when it is desired to drill deeper. During the lifetime of a well a variety of conditions may result in the deterioration of such subsurface piping, including pits, cracks, holes, thin walls, structure changes in the metal and the like. Such deterioration may result from various causes. Electrochemical theory postulates a tendency of steel, or other materials, in an electrolytes environment, such as subsurface formations, to go into solution causing corrosive deterioration. Likewise, during drilling operations drill pipe collars may rub on the inside wall of the pipe causing excessive wear.

There have been various proposals for the design of equipment to measure pipe anomalies while the piping is still in place. One such system which has been widely accepted by the industry is described in U.S. Pat. No. 3,543,144, issued to W. T. Walters et al on Nov. 24, 1970. This system includes an elongated magnetizer assembly including a pair of elongated pole pieces, having a diameter only slightly less than the inside diameter of the piping, and a central core having a magnetizing winding thereon between the pole pieces. A plurality of detectors are positioned between the pole pieces into contact with the interior surface of the casing. A high-intensity unidirectional magnetic field emits from the magnetizing winding with the object of saturating the ferrous piping. If there is no defect in the piping, the magnetic flux lines pass through the piping between the pole pieces. When a defect in the casing exists a portion of the magnetic field will "leak" out of the piping and flow about the defect. This flow is detected within the wall contact detectors.

Yet another system for inspecting oilfield piping is illustrated in U.S. Pat. No. 3,940,689, issued to W. M. Johnson, Jr. on Feb. 24, 1976. This system includes an elongated body member having longitudinally spaced pole pieces magnetically coupled to the ends of an elongated reduced diameter core of magnetic material having a magnetic permeability no greater than the permeability of the pipe to be inspected and a transverse cross sectional area less than the known pipe metal area. A coil wound on the core between the pole pieces generates a unidirectional magnetic flux field and two groups of detectors longitudinally separated on the body member detect flux leakage variations.

While both systems described above have found acceptance in nondestructive testing of subsurface piping they are limited to use in pipe generally in excess of 4.5 inches outside diameter. Accordingly, the present invention provides methods and apparatus for nondestructive testing of the state of deterioration of relatively small diameter subsurface tubing and casing, typically having an outside diameter less than 4.5 inches.

SUMMARY OF THE INVENTION

The present invention provides method and apparatus for the nondestructive inspection of oilfield piping. The method and apparatus utilize a long cylindrical core member disposed between two elongated non-magnetic housing members. Two groups of detector shoes are supported between a pair of arm carriers also serving as pole pieces. A magnetic coil is wound on the core member between the arm carriers. Additional coil assemblies are located on the core member with the arm carriers interposed therebetween. A unidirectional magnetic field emitted by the coil assemblies permeates the casing wall with magnetic lines of flux. Detector shoes detect changes in the magnetic lines of flux caused by defects in the piping.

BRIEF DESCRIPTION OF THE DRAWINGS

FIGS. 1A-1I comprise a longitudinal view, partly in cross section of the instrument assembly in accordance with the present invention.

DETAILED DESCRIPTION OF THE PREFERRED EMBODIMENT

Figure 1E:
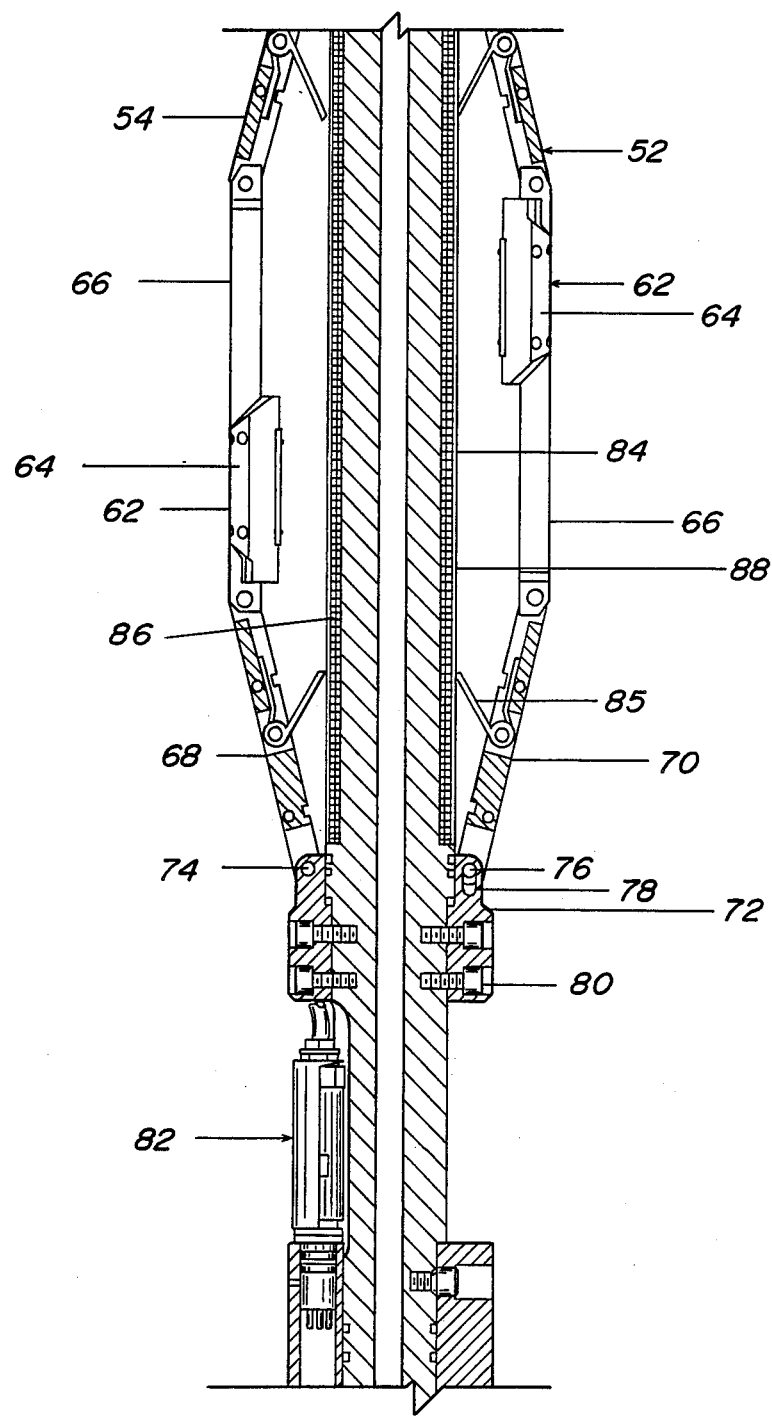
Figure 1F:
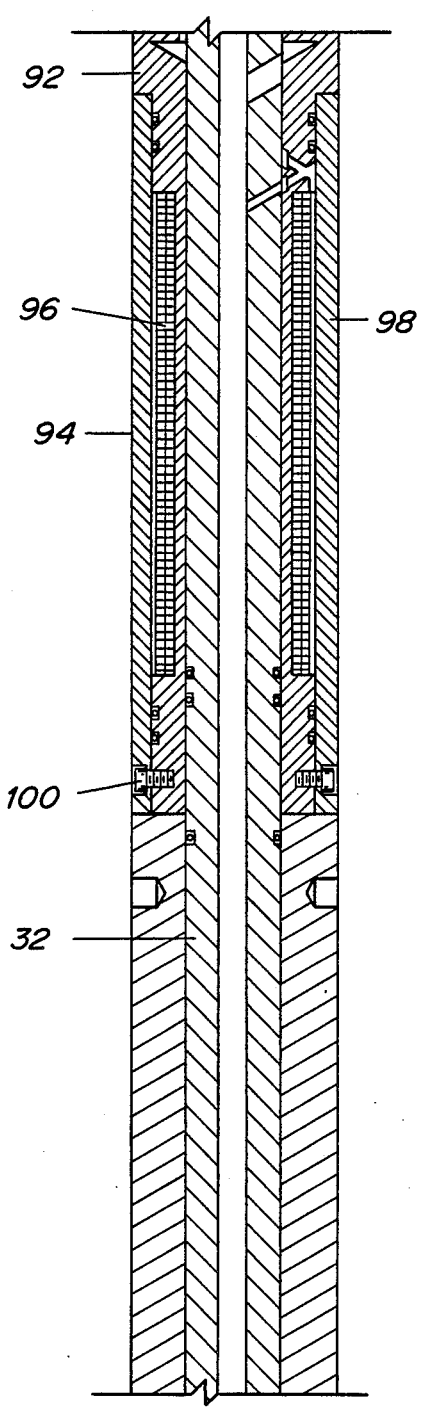
Figure 1G:
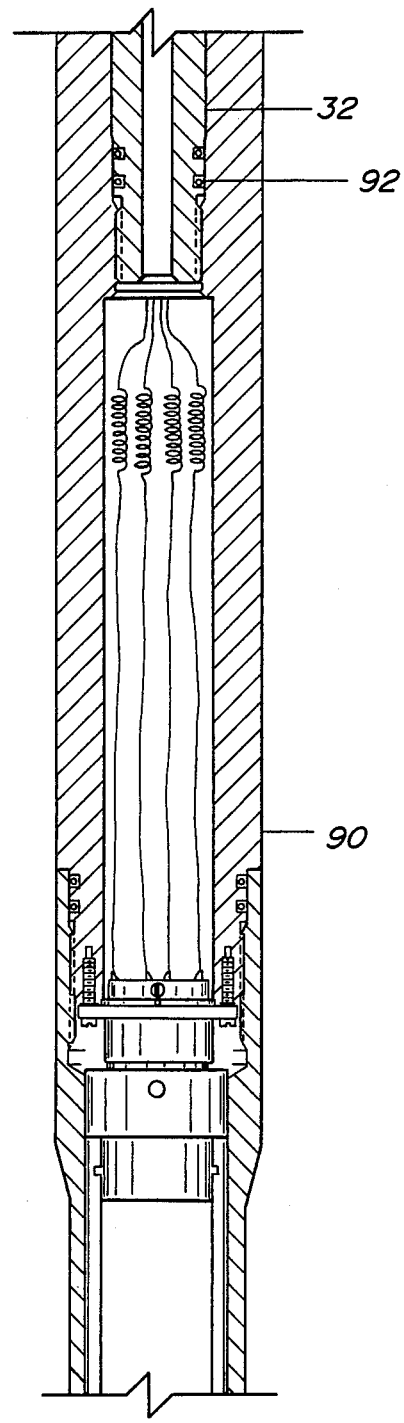

Referring now to FIGS. 1A-1I, there is illustrated inspection instrument 10 in accordance with the present invention. Inspection instrument 10 includes cable connector sub 12 adapted for threadable connection at a first end thereof to the wireline (not shown) common in the art. Housed within cable connector sub 12 is a multi-conductor electrical contact assembly 14 which includes a plurality of electrical connector pins 16 mounted within mounting block 18. Threadably connected to the rear end of contact assembly 14 is electrical cable 20.

Threadably connected to a second end of connector sub 12 is a generally cylindrical, elongated upper housing member 22. Housing member 22 and connector sub 12 are constructed of a suitable non-magnetic material, such as titanium. Retained with the lower end of housing member 22 is electrical connector assembly 24 connected to electrical cable 20. Centralizer member 28, is mounted on the outside of housing member 22.

Coupled to the second end of housing member 22 is a second housing member 26. Housing member 26 is a generally cylindrical member. Second housing member 26 is constructed of a suitable non-magnetic material. Occlusive seal members 30 provide a fluid tight seal between housing member 22 and housing member 26.

Elongated core member 32, constructed of a suitable magnetic material such as iron, is constructed to have an outer diameter slightly less than the inner diameter of housing member 26 and having a centrally located bore therethrough. A first end of core member 32 is retained within housing member 26. Occlusive seal members 34 provide a fluid tight seal between the two members, 32 and 26.

Disposed concentrically about core member 32 is first electrical coil assembly 38. Coil assembly 38 includes a bobbin member 40, constructed of non-magnetic material. Wound on bobbin member 40 is electrical coil 42 covered by coil cover 44, also constructed of a suitable nonmagnetic material, such as titanium. Coil assembly 38 is mounted to core member 32 by suitable means, such as screws 46. Occlusive seal members 37 provide a fluid tight seal.

Arm carrier 48 is concentrically disposed about core member 32. Arm carrier 48 is constructed of a suitable magnetic material and is fixed to core member 32 by suitable retaining means, such as screws 50. A plurality of arm members, illustrated by members 52 and 54, are distributed around the raduis of arm carrier 48. Alternate arm members 52 are pivotally connected to arm carrier 48 by pin 56. The other set of arm members 54 are coupled to arm carrier 48 using a pin member 58 slidably positioned within slot 60 in arm carrier 48.

Pivotally coupled to arm members 52 and 54 are detector shoes 62. Each of the detector shoes 62 includes a detector housing portion 64 and a tang portion 66. The curvature of the outer face of the housing of the detector shoes will approximate the curvature of the inside diameter of the pipe. Within the detector housing portion 64 of each detector shoe 62 is provided a search coil which is of the flux leakage detector type commonly used in the art. This coil intercepts flux perturbations as may be caused by flaws, cracks or other anomalies in the pipe. In addition an eddy current detector coil array is located in the detector housing portion 64. The technique for detection using both flux leakage and eddy current principles is particularly effective for inspection of both inside and outside casing flaws, and is more fully described in U.S. Pat. No. 3,543,144 which is incorporated herein by reference.

Pivotally attached to the other end of detector shoes 64 are arm members, illustrated by members 68 and 70. Alternate arm members 68 are pivotally connected to arm carrier 72 by pivot pin 74. The other set of arm members 70 are coupled to arm carrier 72 using a pin member 76 slidably positioned within slot 78 in arm carrier 72. Arm carrier 72 is radially disposed about core member 32 and is retained thereto by suitable retaining means, such as screws 80. Arm carrier 72 is constructed of a suitable magnetic material. Electrical connector assembly 82 provides electrical connection between electronics package 28 and detector shoes.

With reference to the detector shoe configuration, each detector shoe is mounted between two arm members, for example 52 and 68, and is urged outward against the casing inside wall by spring members 85. Adjacent detector shoes are mounted in opposite directions so that the detector housing portions 64 form a staggered array to assure full 360° scanning of the casing wall circumference. The array of detector shoes define two axially spaced bands of detectors.

Located on core member 32 between arm carriers 48 and 72 is electrical coil assembly 84. Concentrically located about coil 86 is coil cover 88 which is constructed of a layer of suitable non magnetic material, such as titanium.

Disposed concentrically about core member 32 is third electrical coil assembly 94. Coil assembly 94 includes a bobbin member 92, constructed of non-magnetic material. Wound on bobbin member 92 is electrical coil 96 covered by coil cover 98, also constructed of suitable non-magnetic material, such as titanium. Coil assembly 94 is mounted to core member 32 by suitable means, such as screws 100.

Coupled to second end of core member 32 is housing member 90. Housing member 90 is a generally cylindrical member constructed of a suitable non-magnetic material, such as titanium, having subsurface electronics package 110 retained therein, occlusive seal members 92 provide a fluid tight seal between housing member 90 and core member 32. Centralizer members illustrated by 104, are mounted on the outside of housing member 90. Threadably connected to a second end of housing member 90 is connector sub 106. Connector sub 106 includes an electrical connector assembly 108 which allows for electrical connection below instrument 10.

In the operation of the instrument illustrated in FIG. 1, inspection instrument 10 is lowered into the casing. A steady (DC) electromagnetic field of constant strength is generated by main coil 84 and first and second coil assemblies 38 and 94. The coils are arranged in an opposing fashion, the north pole (N) of first coil assembly 38 is directed toward the north pole (N) of main coil 84 and the south pole (S) of third coil assembly 94 is directed toward south pole (S) of main coil 84. As instrument 10 traverses the survey interval, the electromagnetic field produced to saturate the ferromagnetic casing permeates the casing wall with magnetic means of flux. If no defect is present, the flux lines pass from the core 32 and one arm carrier 48, through the casing, and back to the other arm carriers 72. If there is a defect, some of the electromagnetic field will "leak out" of the pipe and flow around the defect. The leakage will be detected by the two sets of detector shoes which survey the casing during the logging pass.

Thus, there has been described and illustrated herein methods for nondestructive testing of small diameter oilfield piping. However those skilled in the art will recognize that many modifications and variations besides those specifically mentioned may be made in the techniques described herein without departing substantially from the concept of the present invention. Accordingly, it should be clearly understood that the form of the invention described herein is exemplary only, and is not intended as a limitation on the scope of the present invention.

The embodiments of the invention in which an exclusive property or privilege is claimed are defined as follows:

1. Apparatus for nondestructive testing of subsurface piping, comprising:
   first and second non-magnetic housing members;
   an elongated magnetic core member having a first end retained within said first housing member and a second end retained within said second housing member;
   first and second arm carrier members coupled to said core member, said arm carriers constructed of magnetic material for magnetic poles;
   first coil assembly coupled to said core member between said first and second arm carrier members for inducing a unidirectional magnetic flux field along a portion of said piping;
   second and third coil assemblies coupled to said core member longitudinally spaced on said core member outside said first and second arm carrier members, respectfuly, for emitting second and third unidirectional magnetic flux fields therefrom, said second and third fields being in opposition to said magnetic flux field from said first coil assembly;
   detector means comprising a plurality of detector shoes coupled to said arm carrier members, said detector means located proximate said first coil assembly and between said second and third coil assemblies, said detector means adapted to contact the interior surface of said piping for sensing alterations in said flux field for indicating defects in said piping.

2. The apparatus of claim 1 wherein said first coil assembly comprises:

an electrical coil wound about said core member; and a non-magnetic cover over said coil.

3. The apparatus of claim 2 wherein said second and third coil assemblies each comprise:
 a bobbin member mounted to said core member;
 an electrical coil winding about said bobbin member;
 a nonmagnetic cover over said coil.

* * * * *